(12) United States Patent
Wang et al.

(10) Patent No.: US 8,217,175 B2
(45) Date of Patent: Jul. 10, 2012

(54) PREPARATION OF OXYMORPHONE FROM ORIPAVINE

(75) Inventors: Peter X. Wang, Chesterfield, MO (US); Tao Jiang, St. Louis, MO (US); Gary L. Cantrell, Troy, IL (US); David Wayne Berberich, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 441 days.

(21) Appl. No.: 12/532,410

(22) PCT Filed: Mar. 14, 2008

(86) PCT No.: PCT/US2008/056929
§ 371 (c)(1),
(2), (4) Date: Sep. 22, 2009

(87) PCT Pub. No.: WO2008/118654
PCT Pub. Date: Oct. 2, 2008

(65) Prior Publication Data
US 2010/0113787 A1    May 6, 2010

Related U.S. Application Data

(60) Provisional application No. 60/896,537, filed on Mar. 23, 2007.

(51) Int. Cl.
*C07D 489/08* (2006.01)
*C07D 489/02* (2006.01)
(52) U.S. Cl. .......................................... 546/45; 546/44
(58) Field of Classification Search .................... 546/45, 546/44
See application file for complete search history.

(56) References Cited

U.S. PATENT DOCUMENTS

| | | | |
|---|---|---|---|
| 2,772,270 A | 10/1954 | Weiss | |
| 3,299,072 A | 10/1963 | Bartels-Keith | |
| 3,393,197 A | 10/1967 | Pachter et al. | |
| 3,468,891 A | 9/1969 | Bartels-Keith | |
| 3,905,981 A | 9/1975 | Olofson et al. | |
| 4,277,604 A | 7/1981 | Dauben et al. | |
| 4,472,253 A | 9/1984 | Schwartz | |
| 4,639,520 A | 1/1987 | Kavka | |
| 4,795,813 A | 1/1989 | Schwartz | |
| 5,071,985 A | 12/1991 | Andre et al. | |
| 5,112,975 A | 5/1992 | Wallace | |
| 5,668,285 A | 9/1997 | Rice et al. | |
| 5,869,669 A | 2/1999 | Huang et al. | |
| 5,922,876 A | 7/1999 | Huang et al. | |
| 5,948,788 A | 9/1999 | Huang et al. | |
| 6,008,354 A | 12/1999 | Huang et al. | |
| 6,008,355 A | 12/1999 | Huang et al. | |
| 6,177,567 B1 | 1/2001 | Chiu et al. | |
| 6,262,266 B1 | 7/2001 | Chiu et al. | |
| 6,365,742 B1 | 4/2002 | Mudryk et al. | |
| 6,376,221 B1 | 4/2002 | Fist et al. | |
| 6,864,370 B1 | 3/2005 | Lin et al. | |
| 7,071,336 B2 | 7/2006 | Francis et al. | |
| 2002/0143183 A1 | 10/2002 | Chiu et al. | |
| 2004/0077863 A1 | 4/2004 | Scammells et al. | |
| 2005/0038250 A1 | 2/2005 | Linders et al. | |
| 2005/0038251 A1 | 2/2005 | Francis et al. | |
| 2006/0173029 A1 | 8/2006 | Chapman et al. | |

FOREIGN PATENT DOCUMENTS

| | | |
|---|---|---|
| WO | WO 2004/108090 | 12/2004 |
| WO | WO 2005/028483 | 3/2005 |
| WO | WO 2008/048711 | 4/2008 |

OTHER PUBLICATIONS

Barber et al., "Synthesis of Thebaine and Oripavine from Codeing and Morphine", Journal of Medicinal chemistry, 1975, 18(11), pp. 1074-1077.
Coop et al., "L-Selectride as a General Reagent for the O-Demethylation and N-Decarbomethoxylation of Opium Alkaloids and Derivatives", J. Org. Chem., 1998, 63, pp. 4392-4396, XP 002485052.
Coop et al., "Direct and Simple O-Demethylation of Thebaine to Oripavine", J. Org. chem.., 1996, 61, p. 6774.
Krassnig et al., "Optimization of the synthesis of oxycodone and 5-methyloxycodone", Archiv der Pharmazia, 1996, 329(6), pp. 325-326.
Ninan et al., "An improved synthesis of noroxymorphone", Tetrahedron, 48(32), 1992, pp. 6709-6716.
Schmidhammer et al., "Synthesis, structure elucidation, and pharmacological evaluation of 5-methyl-oxymorphone . . . ", Helvetica Chimica Acta, 1988, 71(7), pp. 1801-1804.

*Primary Examiner* — Charanjit Aulakh

(57) ABSTRACT

An improved method for the preparation of oxymorphone from oripavine is provided. Oripavine is oxidized to form 14-hydroxymorphinone after which the oxidation reaction is quenched to prevent the formation of 1-1'-dimer side products. The 14-hydroxymorphinone is then reduced, typically by catalytic hydrogenation to form oxymorphone. The inventive method disclosed is further applicable to the production of morphinan derivatives.

27 Claims, No Drawings

PREPARATION OF OXYMORPHONE FROM ORIPAVINE

CROSS REFERENCE TO RELATED APPLICATIONS

This application is a national stage application of PCT/US2008/056929, filed Mar. 14, 2008, which claims the benefit of U.S. Provisional Application No. 60/896,537 filed Mar. 23, 2007.

BACKGROUND OF INVENTION

Oxymorphone and its corresponding 3-OH morphinan derivatives are conventionally produced by O-demethylation of oxycodone. The yield for these reactions varies, typically from 30% to as high as 80%. These reactions are less desirable than alternatives because the oxycodone starting material is expensive.

Alternatively, oxymorphone can be produced by oxidation of oripavine, followed by reduction of the intermediate, as illustrated in Scheme 1:

The route outlined in Scheme 1 is analogous to the method of making oxycodone from thebaine, which is widely practiced in the industry. The use of oripavine is desirable because O-demethylation of oxycodone is avoided. Unfortunately, the use of oripavine is challenging because of its multiple reactive sites by virtue of activating functional groups. The reactions of Scheme 1 yield significant by-products that cannot be easily isolated or removed, resulting in significantly lower reaction yields and purity rendering this synthetic route impractical on a commercial scale.

There exists therefore a need for an improved method of synthesis of oxymorphone and other morphinan derivatives that provides a significant yield improvement, as well as the option of a one-pot synthesis wherein the product is formed in a single reaction vessel without isolating the intermediate.

SUMMARY OF INVENTION

In a non-limiting illustrative aspect of the present invention, there is provided a method comprising oxidizing at least one Formula I compound with an oxidizing agent to form at least one Formula II compound and Formula II-NO compound, wherein an excess portion of the oxidizing agent does not react with the Formula I compound; removing the excess portion of the oxidizing agent; and reducing the Formula II compound and Formula II-NO compound with a reducing agent to form at least one Formula III compound.

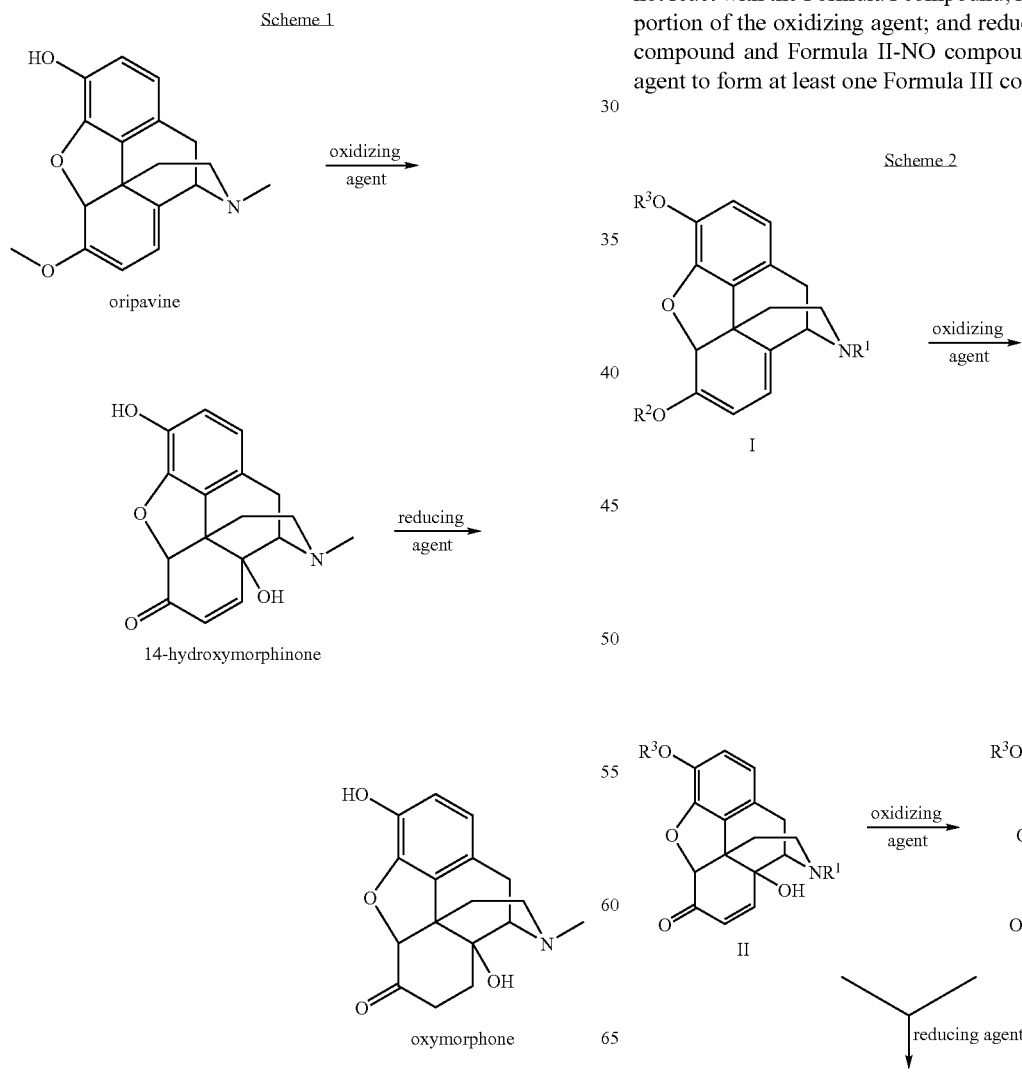

-continued

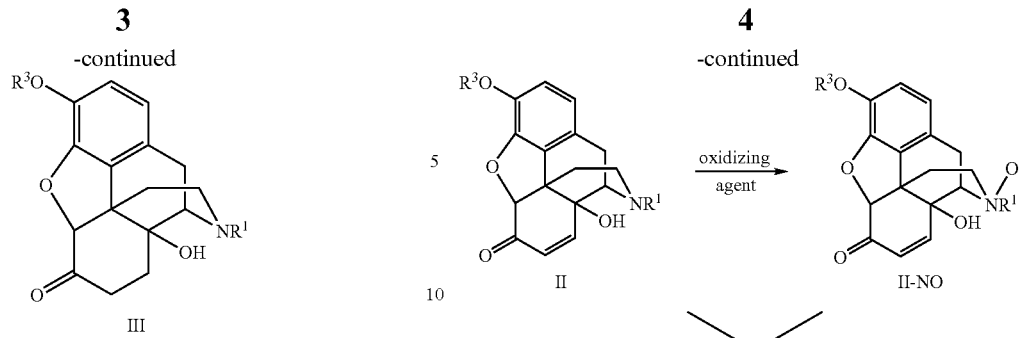

wherein $R^1$, $R^2$ and $R^3$ are independently selected from H, benzyl, 1-8 carbon alkane sulfonyl, p-tosyl, an alkyl group of 1-20 carbons, and a substituted alkyl group, wherein the alkyl group is substituted with a cyclic alkyl group, a phenyl, substituted phenyl, 1-8 carbon alkoxyl or phenoxyl groups.

In another non-limiting illustrative aspect of the present invention, there is provided a method comprising oxidizing a Formula I compound with at least one peroxyacid of the formula $RCO_3H$, wherein R is H, an alkyl group or an aryl group, to form a Formula II compound or Formula II-NO compounds, wherein an excess portion of the peroxyacid does not react with the Formula I compound; neutralizing the excess portion of the peroxyacid $RCO_3H$ with a neutralizing agent to form $RCO_2H$; and catalytically reducing the Formula II compound and Formula II-NO compound with hydrogen in the presence of a transition metal catalyst to form a Formula III compound.

In another non-limiting illustrative aspect of the present invention, there is provided a method for producing oxymorphone comprising oxidizing oripavine with a peroxyacid acid $RCO_3H$, wherein R is H, an alkyl group or an aryl group, to form 14-hydroxymorphinone and 14-hydroxymorphinone N-oxide, wherein an excess portion of the peroxyacid does not react with the oripavine; neutralizing the excess portion of the peroxyacid with a neutralizing agent; and catalytically hydrogenating the 14-hydroxymorphinone with a reducing agent to form oxymorphone.

DETAILED DESCRIPTION

There is therefore disclosed an improved method for the synthesis of oxymorphone and morphinan derivatives from oripavine and its derivatives, respectively.

The reaction illustrated in Scheme 1 applies more generally to morphinan compounds as illustrated in Scheme 2:

Scheme 2

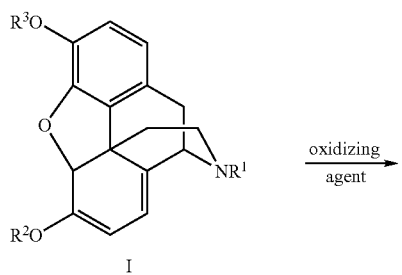

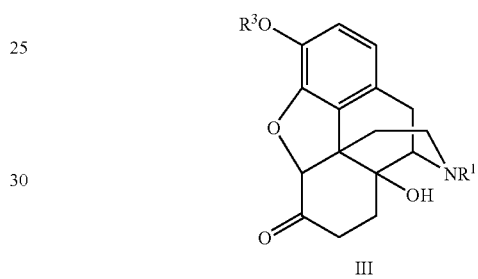

wherein $R^1$, $R^2$ and $R^3$ are independently selected from H, benzyl, 1-8 carbon alkane sulfonyl, p-tosyl, an alkyl group of 1-20 carbons, and a substituted alkyl group, wherein the alkyl group is substituted with a cyclic alkyl group, a phenyl, substituted phenyl, 1-8 carbon alkoxyl or phenoxyl groups.

The formulas and compounds disclosed and claimed herein are intended to further include the common salts of the formulas and compounds, as is well known in the art.

The term alkyl groups, as used throughout this disclosure, refers to any alkyl group that does not interfere sterically with the reaction, and includes straight chain, branched, substituted and cyclic alkyl groups.

The significant by-products responsible for the conventional synthesis low yields have been isolated and identified. The first step of Scheme 2, reacting a Formula I compound (oripavine wherein $R^1$ and $R^2$=methyl, $R^3$=H) with at least one oxidizing agent to form Formula II (14-hydroxymorphinone wherein $R^1$=methyl and $R^3$=H), typically occurs within about 30 minutes. Any unreacted, excess portion of the oxidizing agent further oxidizes the Formula II compound to form the N-oxide Formula II-NO, at a slower rate than the initial oxidation. The excess portion of oxidizing agent, in combination with a metal catalyst, also results in the formation of 1-1'-dimers according to Formula IV, V and VI, as illustrated in Scheme 3. The reduction reaction of these dimers may further proceed to form the 1-1'-dimer according to Formula VII.

Scheme 3

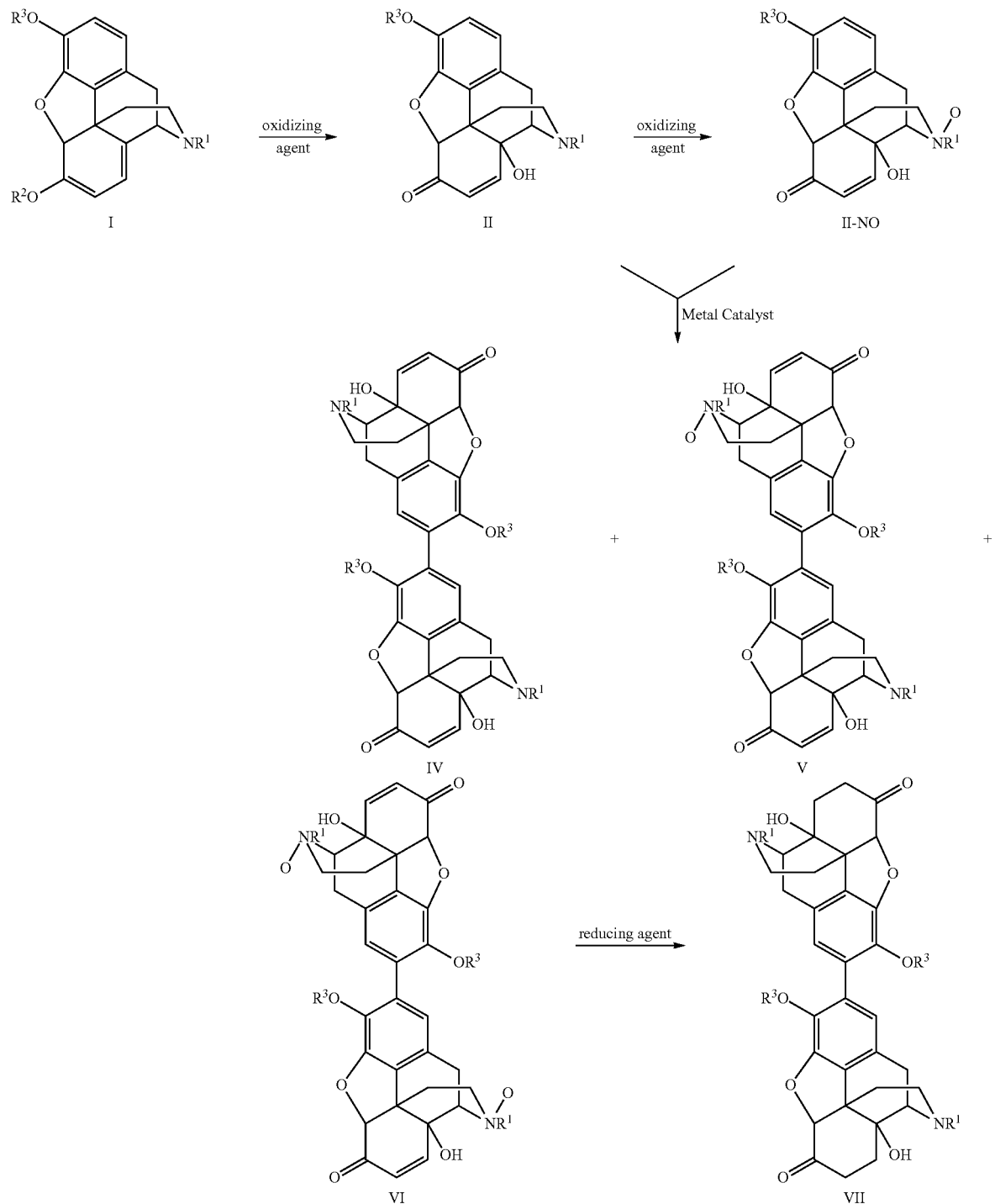

The 1-1'-dimers defined herein are more insoluble than oxymorphone, and are therefore difficult to remove by recrystallization. Further, repeated crystallization often results in decomposition of the product. These side products are significant, as much as 15% to 20% of the yield, and are the primary reason that the production of oxymorphone using oripavine as a starting material has been heretofore impractical on a commercial scale. However, a method which would reduce or eliminate the formation of 1-1'-dimers would not only provide a commercially viable synthesis, but would allow for a practical one-pot synthesis, since the 14-hydroxymorphinone intermediate would not have to be isolated.

It has been unexpectedly determined that quenching the oxidation reaction by the removal of any excess portion of oxidizing agent prior to the addition of the reducing agent prevents the formation of 1-1'-dimers. This inventive method is illustrated in Scheme 4. It is noted that any N-oxide side product (II-NO) formed by the oxidizing agent is also reduced to Formula III, as described above. By introducing a reaction condition that removes any excess oxidizing agent prior to addition of the reducing agent, the present method provides a high yield, commercially viable one-pot synthesis. Further, since this reaction is analogous to the conventional production of oxycodone from thebaine as described in the literature, the instant process can be accomplished with standard production equipment.

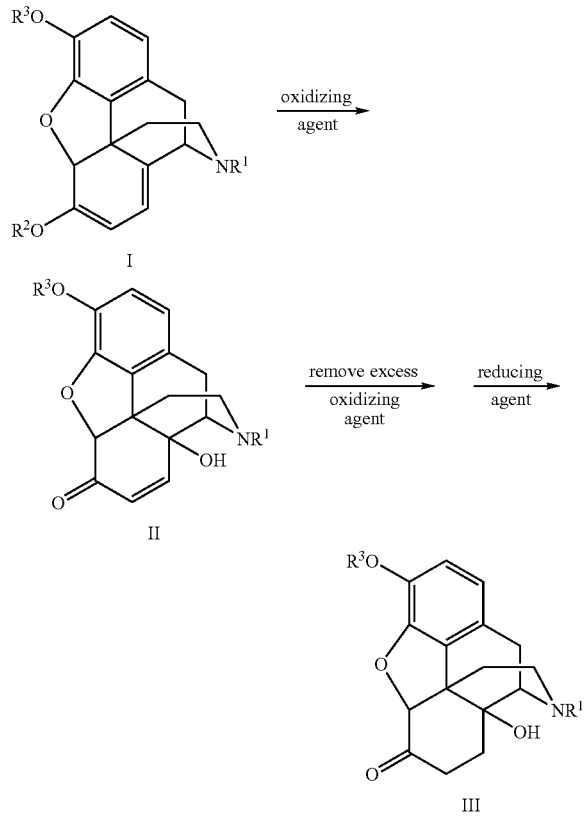

Scheme 4

The method of oxidizing the Formula I compound may be any conventional oxidizing method as are well known in the art. Typically the Formula I compound is dissolved in a solvent, to form a reaction mixture. Suitable solvents include any solvent capable of dissolving oripavine, as is well known in the art, and include HOAc, HOAc/water, $R^5CO_2H$, $R^5CO_2H/H_2O$, $R^5CO_2H/H_2O/R^6OH$, $R^5CO_2H/H_2O/THF$, inorganic acid/$H_2O$, inorganic acid/$H_2O/R^6OH$, inorganic acid/$H_2O/THF$ and mixtures thereof, wherein $R^5$ and $R^6$ are independently selected from H, an alkyl group of 1-20 carbons, preferably 1-8 carbons, and aryl group. Suitable inorganic and organic acids include HCl, $H_2SO_4$, $H_3PO_4$, $MeSO_3H$, toluenesulfonic acid and mixtures thereof. Illustrative oxidizing agents include peroxyacids or mixtures thereof.

The Formula II compound is formed quantitatively when one equivalent of at least one peroxyacid of the formula $R^7CO_3H$, wherein $R^7$ is selected from H, an alkyl of 1-20 carbons, more preferably 1-8 carbons, or an aryl group. The peroxyacid is added under acidic conditions, less than about pH 7, typically pH 0 to pH 6, with about pH 2 to about pH 4 being preferred.

Suitable peroxyacids include $HCO_3H$, $CH_3CO_3H$, m-$ClC_6H_4CO_3H$, $C_6H_4CO_3H$ and mixtures thereof.

If oripavine is oxidized with peroxyacid, and followed by catalytic hydrogenation without adding a reagent to quench the excess peroxyacid or hydrogen peroxide or other oxidation reagents, the ratio of peroxyacid or hydrogen peroxide or other oxidation reagents to Formula I compound in the reaction mixture influences the oxidation rate and product purity. As is seen in Table 1, as the weight ratio of peroxyacid to oripavine used increases from 0.70 g in Entry 1 to 0.85 g in entry 3, the percentage of bisoxymorphone produced rose from 7% to 25%, respectively. The table illustrates the importance of this invention in reduction of dimer impurities.

TABLE 1

| Entries | $CH_3CO_3H$ added | Oxymorphone: bisoxymorphone |
|---|---|---|
| 1 | 0.70 gram per gram of oripavine | 86:7 |
| 2 | 0.78 gram per gram of oripavine | 89:10 |
| 3 | 0.85 gram per gram of oripavine | 73:25 |

The oxidation reaction preferably takes place at a temperature above which the solvent freezes, typically about 0° C. to 10° C., and below which the production of side-products increases, typically about 40° C. to 50° C. The pH of the oxidation reaction mixture is maintained high enough to prevent oxidation of the double bond from becoming significant, and low enough to prevent a significant amount of the N-oxide derivative (and phenoxyl group when $R^3$=H) from being produced. The pH therefore is typically from about pH 2 to pH 4.

In the method of the present invention, any oxidizing agent that is not consumed by the oxidation reaction is considered the excess or unreacted portion; for example, unreacted peroxyacid. The excess oxidizing agent is removed from the reaction mixture, thereby quenching the oxidizing reaction prior to the addition of the metal catalyst to convert the Formula II intermediate (14-hydroxymorphinone wherein $R^1$=methyl, $R^3$=H) into the Formula III product (oxymorphone wherein $R^1$=methyl, $R^3$=H.)

The oxidizing agent excess portion may be removed or neutralized by any suitable method known in the art, including addition of a neutralizing agent (which reduces the oxidizing agent), electric reduction, thermo-decomposition of the oxidizing agent, and combinations thereof. The excess portion would include the oxidizing agent, or oxidant, as well as any other oxidant present in the reaction mixture as a side-product or impurity, such as $H_2O_2$. In an illustrative example wherein the oxidizing agent is a peroxyacid, the neutralizing agent is a peroxyacid reducing reagent that can react with the peroxyacid and to reduce $R^7CO_3H$ to $R^7CO_2H$, wherein $R^7$ is an H, alkyl or substituted alkyl group, as defined above.

Suitable neutralizing agents for this step include $H_2C_2O_4$, hypophosphorous acid, formic acid, citric acid, ascorbic acid, $NaNO_2$, $NaS_2O_4$, $Na_2SO_3$, salts of hydrazine, $R^8CHO$ (wherein $R^8$ is selected from H, alkyl of 1-20, more preferably 1-8 carbons, or a phenyl or substituted phenyl group) sulfur dioxide, sodium hydrosulfite, formaldehyde sulfoxylate, diimide, hydrazine, hypophosphorous, triphenylphosphine and mixtures thereof.

Unexpectedly, the reaction of the peroxyacid reducing agent does not have significant reductive effect on the intermediate (14-hydroxymorphinone wherein $R^1$=methyl, $R^3$=H).

After the excess oxidizing agent is neutralized with the peroxyacid reducing agent, the intermediate Formula II compound (14-hydroxymorphinone wherein $R^1$=methyl, $R^3$=H) may be converted/reduced to the product of Formula III (oxymorphone wherein $R^1$=methyl, $R^3$=H) by reductive methods well known in the art. Typically, hydrogen in the presence of at least one transition metal catalyst is utilized as the catalytic reducing agent in a catalytic hydrogenation reaction. Suitable transition metal catalysts include Pd/C, Pt/C, Ru/C, Rh/C, Ir/C, Ni/C, $PtO_2$, Raney Ni, Wilkinson's Catalyst and mixtures thereof.

In an illustrative example, the method of the present invention provides an improved method for the synthesis of oxymorphone from oripavine. Oripavine is added while stirring to a solvent such as $AcOH/H_2O$ to form a reaction mixture. The reaction mixture is cooled to about 5° to about 10° C. and kept in an ice bath while $CH_3CO_3H$ is added as an oxidizing agent to convert the oripavine to 14-hydroxymorphinone. The reaction of oripavine with peroxyacetic acid forms 14-hydroxymorphinone, and may include the 14-hydroxymorphinone N-oxide derivative. Any excess, unreacted peroxyacetic acid is removed/neutralized by the addition of ascorbic acid. The reaction mixture is then catalytically hydrogenated with Pd/C to produce oxymorphone. The addition of ascorbic acid as a neutralizing agent to quench the oxidation reaction prevents the formation of 1-1'-dimer by products, increasing the yield of oxymorphone. The typical yield of oxymorphone produced utilizing the method of the present invention is typically greater than 80%, preferably greater than 90%, and most preferably greater than 95%.

The yield improvement of the present invention is illustrated in Table 2. Entry 1, formed according to Example 6 herein (without addition of quenching reagent), shows 30% dimer produced by the oxidation reaction, and 28% after subsequent reduction reaction. Entry 2, according to Example 7 herein (with addition of quenching reagent, in this example ascorbic acid), shows 1% 1-1'-dimer after the oxidation reaction with quenching, and 2% 1-1'-dimer after the reduction reaction. Under optimal conditions, ratios of 1-1'-dimer to oxymorphone of less than 0.1% have been observed.

TABLE 2

| Entries | Sum of 14-OH-morphinone derivatives:sum of bis-14-OH-morphinone derivatives | Oxymorphone: bisoxymorphone |
|---|---|---|
| 1 | 30:67 | 28:69 |
| 2 | 97:1 | 93:2 |

In an alternate embodiment of the present invention, it has further been discovered that the percentage of the Formula II-NO formed can be increased, if desired, by manipulating the reaction conditions. The Formula II-NO compound (14-hydroxymorphinone N-oxide wherein $R^1$=methyl) was formed as the main product when an excess of at least two equivalences of the oxidizing agent was added to the Formula I compound (oripavine wherein $R^1$ and $R^2$=methyl, $R^3$=H) or at least one equivalent of the oxidizing agent was added to the Formula II compound (14-hydroxymorphinone wherein $R^1$=methyl, $R^3$=H).

In an illustrative example of the formation of an N-oxide, excess peroxyacetic acid is added to oripavine as an oxidizing agent, resulting in 14-hydroxymorphinone N-oxide as the primary product. The compound 14-hydroxymorphinone N-oxide can then be converted to oxymorphone by catalytic hydrogenation.

In another alternative embodiment the reaction conditions can be manipulated to increase the percentage of 1-1'-dimers of Formula IV, V and VI formed, if desired. It has been determined that the presence of both excess oxidation reagent as well as excess metal catalyst in the conventional reaction illustrated in Scheme II will increase the percentage of 1-1'-dimers formed. Further, it has been determined that the ratio of 1-1'-dimers to the Formula III product increases as the excess oxidation reagent increases in the presence of the same amount of metal catalyst.

Illustrative examples of the formation of 1-1'-dimers include; the formation of Bis-14-hydroxymorphinone by the dimerization of 14-hydroxymorphinone in the presence of both peroxyacid and a transition metal catalyst; the formation of Bis-14-hydroxymorphinone-N-oxide by the dimerization of 14-hydroxymorphinone N-oxide in the presence of both peroxyacid and a transition metal catalyst; and the formation of 1,1'-dimer of 14-hydroxymorphinone and 14-hydroxymorphinone-N-oxide by a mixed dimerization of 14-hydroxymorphinone and 14-hydroxymorphinone N-oxide in the presence of both peroxyacid and a transition metal catalyst. In each of these examples, the peroxyacid may be at least one $R^7CO_3H$, wherein $R^7$ is selected from H, alkyl and substituted alkyl groups, as defined above, and the transition metal catalyst may be Pd/C, Pt/C, Ru/C, Rh/C, Ir/C, Ni and mixtures thereof.

EXAMPLES

Example 1

Preparation of 14-hydroxymorphinone

To a 200 mL flask, dried oripavine (10.00 g, 95% wt/wt %) was dissolved in $HOAc/H_2O$ (1:4, 100 mL) and cooled to 5° C. to 10° C. Peroxyacetic acid, $CH_3CO_3H$, (9.1 mL, 32% wt/wt %) was added over 3 minutes and the reaction mixture was stirred at 5° C. to 10° C. for 30 minutes. HPLC data showed that the reaction was completed. The reaction mixture was allowed to warm to 25° C. for 30 minutes. $H_2C_2O_4$ (3.0 g) was added to the reaction mixture, and was stirred at room temperature for 30 minutes and then heated to 50° C. for 30 minutes. The solution was assayed by HPLC and >99% conversion was observed.

Example 2

Preparation of Oxymorphone

To the solution produced in Example 1, 1.0 g 10% Pd/C was added and stirred for 10 minutes. The flask was under vacuum and nitrogen filling for 4 times. It was then under vacuum and hydrogen filling for 4 times. The mixture was stirred under hydrogen (60 PSI) at 80° C. for 3 hours. The mixture was cooled to room temperature and filtered. The resulting solid residue was washed with the solution of $HOAc/H_2O$ (1:4, 20 mL.) The solution was assayed by HPLC and >99% conversion from 14-hydroxymorphinone was observed. The yield for the product in the solution before the isolation was 95% from oripavine to oxymorphone. The purity of oxymorphone is >97% (peak area %) and the ratio of oxymorphone to bis-1,1'-oxymorphone is >99:1. The solution was extracted with $CHCl_3$ (2×10 mL) and then heptane (15 mL). The aqueous layer was cooled to 0° C. to 10° C. 55 mL of KOH (50% wt/wt % in water) was added slowly and the pH of the mixture was adjusted to 8-9. The reaction temperature was maintained at <30° C. during the addition. A precipitate was formed as the reaction mixture was stirred at 0° C. to 10° C. for 1 hour before filtering. The solid was washed with water (3×15 mL), and dried to give 6.15 g product. The combined filtrate and washes contained 2.4 g of product, measured by HPLC.

Example 3

Entry 1 of Table 1

Oripavine (10 g) was dissolved in HOAc/H$_2$O (2:3, 50 mL, 5.0 mL per g of oripavine). CH$_3$CO$_3$H (32% wt/wt) (7.0 g, 0.7 g/g or oripavine) was added to the oripavine solution and stirred at 10° C. for 5 minutes. 5% Pd/C (1.0 g, 0.1 g per g of oripavine) was added to the reaction mixture under hydrogen (60 psi) at room temperature for 60 min, and then the temperature was raised to 80° C. for 1.5 hour.

Example 4

Entry 2 of Table 1

Oripavine (10 g) was dissolved in HOAc/H$_2$O (2:3, 50 mL, 5.0 mL per g of oripavine). CH$_3$CO$_3$H (32% wt/wt) (7.8 g, 0.78 g/g or oripavine) was added to the oripavine solution and stirred at 10° C. for 5 minutes. 5% Pd/C (1.0 g, 0.1 g per g of oripavine) was added to the reaction mixture under hydrogen (60 psi) at room temperature for 60 min, then raised to 80° C. for 1.5 hours.

Example 5

Entry 3 of Table 1

Oripavine (10 g) was dissolved in HOAc/H$_2$O (2:3, 50 mL, 5.0 mL per g of oripavine). CH$_3$CO$_3$H (32% wt/wt) (8.5 g, 0.85 g/g or oripavine) was added to the oripavine solution and stirred at 10° C. for 5 minutes. 5% Pd/C (1.0 g, 0.1 g per g of oripavine) was added to the reaction mixture under hydrogen (60 psi) at room temperature for 60 min, then raised to 80° C. for 1.5 hours.

Example 6

Entry 1 of Table 2

Oripavine (2.0 g) was dissolved in HOAc/H$_2$O (2:3, 20.0 mL). CH$_3$CO$_3$H (32% wt/wt, 1.33 mL) was added to the oripavine solution. The resulting reaction mixture was stirred at room temperature for 15 minutes. 5% Pd/C (0.2 g) was added to the reaction mixture under hydrogen (60 psi) at room temperature for 60 min, and then the temperature was raised to 80° C. for 1.5 hours.

Example 7

Entry 2 of Table 2

Oripavine (2.0 g) was dissolved in HOAc/H$_2$O (2:3, 20 mL). CH$_3$CO$_3$H (32% wt/wt, 1.33 mL) was added to the oripavine solution, followed by the addition of ascorbic acid (1.2 g). The resulting reaction mixture was stirred at room temperature for 15 minutes. 5% Pd/C (0.1 g per g of oripavine) was added to the reaction mixture under hydrogen (60 psi) at room temperature for 60 min, and then the temperature was raised to 80° C. for 1.5 hours.

Example 8

Preparation of Oxymorphone Using Ascorbic Acid to Neutralize Excess Peroxyacetic Acid or Hydrogen Peroxide HOAc (30 mL) and water (120 mL) were added to a 250 mL flask (pH=2.6, ~150 mL). With the agitator on, oripavine (30.00 g, assayed to be 96% wt/wt, containing oripavine 97 mmol) was charged to the flask (final pH=3.66). Heat was released and the final solution reached 25° C. from 20° C., pH=3.66. The reaction mixture was cooled to 5° C. to 10° C., and, CH$_3$CO$_3$H (23.4 g, containing 33% wt/wt peroxyacetic acid and 5.34% H$_2$O$_2$ containing 97 mmol peracetic acid) was added over 10 minutes. Heat was released during the addition and the reaction temperature was maintained below 15° C. (primarily 10° C. to 15° C.) during the addition by ice water bath. The cooling bath was removed after the addition was completed. The temperature of the reaction mixture was 10° C. at this point. The reaction mixture was stirred for another 30 minutes after cooling bath was removed and the final temperature reached 15° C. Ascorbic acid (1.5 g) was added to the reaction mixture. The solution was heated to 35° C. over a 30 minute period and maintained at 35° C. for 1 hour afterwards. The reaction mixture was transferred to a pressure bearing flask (350 mL) for the reduction reaction. The flask for the oxidation was washed with the 2% HOAc (v/v; 2×7.5 mL). The washes were transferred to the reduction flask. 1.0 g of 10% Pd/C was added and the flask was pump/purged first with nitrogen and then with hydrogen each 4 times. The flask was cycled under vacuum and hydrogen 4 times. The reaction mixture was stirred under hydrogen (60 PSI) at 85° C. to 90° C. (90° C. oil bath) for 4.5 hours. The reaction mixture was cooled down to 35° C. and filtered. The recovered solid was washed with a solution of 2% HOAc/H$_2$O (v/v, 3×15 mL). Yield of oxymorphone formed in the solution was calculated by HPLC analysis: 95%.

Example 9

Preparation of Oxymorphone Using NaHSO$_3$ to Neutralize Excess Peroxyacetic Acid HOAc (30 mL) and water (120 mL) were added to a 250 mL flask (pH=2.6, ~150 mL). With stirring, oripavine (30.00 g, assayed to be 96% wt/wt, containing 97 mmol oripavine) was charged to the flask (final pH=3.6). Heat was released and the final solution reached 25° C. from 20° C., pH=3.6. The reaction mixture was cooled to 5° C. to 10° C. and nitrogen was turned on. CH$_3$CO$_3$H (23.4 g, 32% wt/wt, 33.1% titrated with sodium thiosulfate, containing 5.34% H$_2$O$_2$, contains 97 mmol peracetic acid) was added over 10 minutes Heat was released during the addition and the reaction temperature was maintained below 15° C. (10° C. to 15° C.) by ice water bath during the addition. The ice bath was removed and the reaction mixture was stirred for another 30 minutes. The reaction mixture was warmed to 20° C. to 25° C. and stirred for another 30 minutes. NaHSO$_3$ (1.5 g) was added and the solution was heated to 35° C. and maintained at 35° C. for 1 hour The reaction mixture was transferred to a pressure bearing flask (350 mL flask) for reduction reaction. The flask for the oxidation was washed with the 2% HOAc (v/v; 2×7.5 mL). The washes were transferred to the reduction flask. 1.0 g of 10% Pd/C was added and the flask was pump/purged first with nitrogen and then with hydrogen. The flask was cycled under vacuum and hydrogen filling 4 times. The mixture was stirred under hydrogen (60 PSI) at 85° C. to 90° C. (90° C. oil bath) for 4.5 hours. The reaction mixture was cooled to 35° C. and filtered. The recovered solid was washed with a solution of 2% HOAc/H$_2$O (v/v, 3×15 mL). The solution weighed 252.59 g, 0.7057 g of the original solution was taken and diluted to 50.0 mL for HPLC analysis. The calculated yield was 95%.

Example 10

Preparation of Oxymorphone Using Oxalic Acid, H$_2$C$_2$O$_4$, to Neutralize Excess Peroxyacetic Acid Glacial acetic acid, HOAc, (30 mL) and water (120 mL) were added to a 250 mL flask (pH=2.6, ~150 mL). With the stirring mechanism on, oripavine (30.00 g, assayed to be 96% wt/wt, containing oripavine 97 mmol) was charged to the flask. Heat was released and the final solution reached 25° C. from 20° C., pH=3.66. The reaction mixture was cooled to 5~10° C., and, CH$_3$CO$_3$H (23.4 g, containing 33% wt/wt peroxy acetic acid and 5.34% H$_2$O$_2$, 97 mmol peracetic acid) was added over 10 minutes. The reaction mixture was stirred for another 30 minutes after cooling bath was removed and the final temperature reached 15° C. H$_2$C$_2$O$_4$ (1.5 g) was added to the reaction mixture, and the solution was heated to 35° C. over a 30 minute period and maintained at 35° C. for 1 hour. The reaction mixture was transferred to a pressure bearing flask (350 mL) for the reduction reaction. The flask for the oxidation was washed with the 2% HOAc (v/v; 2×7.5 mL). The washes were transferred to the reduction flask. 1.0 g of 10% Pd/C was added and the flask was pump/purged first with nitrogen and then with hydrogen each 4 times. The flask was cycled under vacuum and hydrogen 4 times. The reaction mixture was stirred under hydrogen (60 PSI) at 85° C. to 90° C. (90° C. oil bath) for 4.5 hours. The reaction mixture was cooled down to 35° C. and filtered. The recovered solid was washed with a solution of 2% HOAc/H$_2$O (v/v, 3×15 mL). Yield of oxymorphone formed in the solution was calculated by HPLC analysis: 95%.

Example 11

Preparation of Oxymorphone Using Thermo-Decomposition to Neutralize Excess Peroxyacetic Acid HOAc (30 mL) and water (120 mL) were added to a 250 mL flask (pH=2.6, ~150 mL). With the stirring mechanism on, oripavine (30.00 g, assayed to be 96% wt/wt, containing oripavine 97 mmol) was charged to the flask. Heat was released and the final solution reached 25° C. from 20° C., pH=3.66. The reaction mixture was cooled to 5~10° C., and, CH$_3$CO$_3$H (23.4 g, containing 33% wt/wt peroxy acetic acid and 5.34% H$_2$O$_2$, 97 mmol peracetic acid) was added over 10 minutes. The reaction mixture was stirred for another 30 minutes after cooling bath was removed and the final temperature reached 15° C. The solution was heated to 55° C. over a 30 minute period and maintained at 55° C. for 1 hour. The reaction mixture was transferred to a pressure bearing flask (350 mL) for the reduction reaction. The flask for the oxidation was washed with the 2% HOAc (v/v; 2×7.5 mL). The washes were transferred to the reduction flask. 1.0 g of 10% Pd/C was added and the flask was pump/purged first with nitrogen and then with hydrogen each 4 times. The flask was cycled under vacuum and hydrogen 4 times. The reaction mixture was stirred under hydrogen (60 PSI) at 85° C. to 90° C. (90° C. oil bath) for 4.5 hours. The reaction mixture was cooled down to 35° C. and filtered. The recovered solid was washed with a solution of 2% HOAc/H$_2$O (v/v, 3×15 mL). Yield of oxymorphone formed in the solution was calculated by HPLC analysis: 85%.

Example 12

A Standard Procedure on Making Oxymorphone from Oripavine

The following procedure was practiced multiple times in lab on a 30 g scale. Dried oripavine (30 g) was used for the calculation of the reagents needed for the reaction.
Oxidation of Oripavine:
HOAc (0.5 mL per g of oripavine) and water (4.5 mL per g of oripavine) were added to a flask (pH=2.6) and stirring begun. The dried oripavine (assayed to be 96% wt/wt) was charged to the flask. Heat was released and the final solution reached to 25° C. from 20° C., pH=3.6. The resulting reaction mixture was cooled to 5° C. to 10° C. and nitrogen sweep was initiated. To the reaction mixture, CH$_3$CO$_3$H (32% wt/wt, 0.78 g per g of oripavine) was added over 10 to 30 minutes. Heat was released during the addition and the reaction temperature was maintained below 15° C. (10° C. to 15° C. most of the time) using an ice water bath during the addition. The ice bath was removed and the reaction mixture was stirred for another 60 minutes. Ascorbic acid (0.05 g per g of oripavine) was added. The reaction mixture was heated to 35° C. and maintained at 35° C. for 1 hour. The reaction mixture was transferred to a pressure bearing flask for hydrogenation. The flask for the oxidation was washed with the 2% HOAc (v/v; 2×0.25 mL per g of oripavine). The washes were transferred to the hydrogenation flask.
Reduction of 14-Hydroxymorphinone:
10% Pd/C (0.15 g per g of oripavine) was added. The flask was pump/purged first with nitrogen and then with hydrogen four times. It was then placed under vacuum and hydrogen filled four times. The mixture was stirred under hydrogen (60 PSI) at 85° C. to 90° C. (90° C. oil bath) for 4.5 hours. Proceed if HPLC shows that the reduction is complete (14-OH-morphine <or =0.1%). Additional 10% Pd/C (0.1 g per g of oripavine) was added and the operation was repeated if HPLC showed that the reduction was not complete (14-OH-morphine >0.1%). The mixture was cooled to 35° C. and filtered. The resulting solid was washed with a solution of 2% HOAc/H$_2$O (v/v, 3×0.5 mL per g of oripavine).
Isolation of Oxymorphone as Crude Product:
To the above filtrate, NaHSO$_3$ (0.1 g per g of oripavine) was added and nitrogen sweep was initiated. 50% Sodium Hydroxide, NaOH, (1.33 g per g of oripavine) was charged (pH=about 6.6). Temperature reached 35° C. during charging. The pH was adjusted with additional 50% NaOH (~0.15 mL per g of oripavine) to 7.0. Note: The pH value would take 3 to 5 minutes to become steady. The pH adjustment was repeated until the pH change was within +/−0.2 over 5 minutes. The pH was adjusted to 6.6 to 7.0 with 50% NaOH or HOAc if necessary. The solution was heated and stirred at 38° C. (35° C. to 80° C.) for 2 hours to form a light brown solution (pH changed within +/−0.2). The solution was cooled to room temperature (20° C.). Concentrated ammonium hydroxide, c-NH$_4$OH, (0.5 mL per g of oripavine) was added to form a precipitate (pH=9.0 to 10.0). The mixture was stirred at room temperature for 2 hours. The mixture was filtered, and the resulting solid was washed with water (3×1 mL per g of oripavine). The solid was dried under flowing air at room temperature for 1 hour to give product as a tan solid.

Purification of Oxymorphone:

The wet cake was charged to a flask. Water (8×1 g per g of oripavine) was charged. Agitation was turned on and nitrogen sweep was initiated. c-HCl (0.3 mL per g of oripavine) was added to form a solution (pH=about 4 to 5). A charcoal treatment and filtration was conducted when the color was dark. c-NH$_4$OH (~1 mL per g of oripavine) was added to adjust pH=about 9 to 10 to form a precipitate. The mixture was stirred at room temperature for 1 hour, then was filtered and washed with water (5×1 mL per g of oripavine). The resulting solid was dried under flowing air at room temperature or 1 hour to give a solid. The solid was further dried under house vacuum at 75° C. for 16 hours to give the product as a tan solid. The weight of solid should range from 0.8 g to 1.0 g per g of oripavine with peak area >95%, wt/wt 90 to 95% and water content 3 to 5%.

Having described the invention in detail, those skilled in the art will appreciate that modifications may be made of the invention without departing from its' spirit and scope. Therefore, it is not intended that the scope of the invention be limited to the specific embodiments described. Rather, it is intended that the appended claims and their equivalents determine the scope of the invention.

The invention claimed is:

1. A method comprising:
   a) oxidizing at least one Formula I compound with a peroxyacid oxidizing agent to form an oxidation reaction mixture comprising at least one Formula II compound and Formula II-NO compound;
   b) quenching the oxidation reaction mixture by removing an excess portion of the oxidizing agent, wherein the excess portion of the oxidizing agent is oxidizing agent that does not react with the Formula I compound; and
   c) reducing the Formula II compound and Formula II-NO compound with a reducing agent to form at least one Formula III compound,

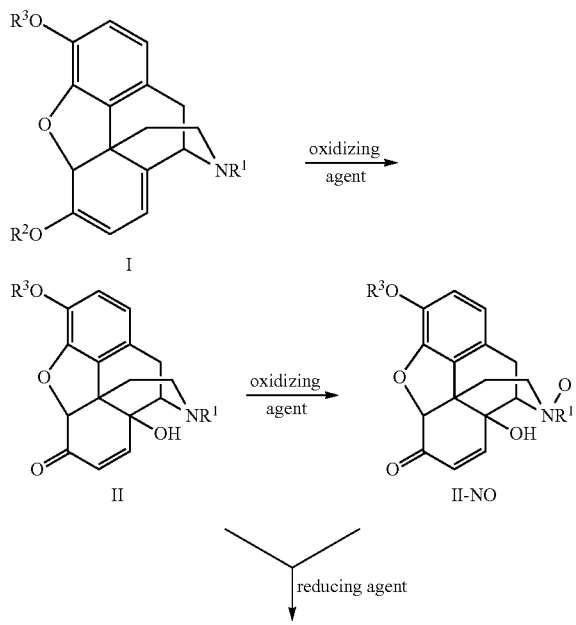

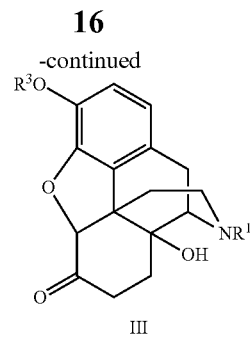

wherein R$^1$, R$^2$ and R$^3$ are independently selected from H, benzyl, 1-8 carbon alkane sulfonyl, p-tosyl, an alkyl group of 1-20 carbons, and a substituted alkyl group, wherein the alkyl group is substituted with a cyclic alkyl group, a phenyl, substituted phenyl, 1-8 carbon alkoxyl or phenoxyl groups.

2. The method of claim 1 wherein the Formula III compound formed represents greater than an 80% yield.

3. The method of claim 1 wherein the Formula III compound formed represents greater than a 90% yield.

4. The method of claim 1 wherein the Formula III compound formed represents greater than a 95% yield.

5. The method of claim 1 wherein the oxidizing agent includes at least one peroxyacid of the formula RCO$_3$H, wherein R is H, an alkyl group of 1-20 carbons or an aryl group.

6. The method of claim 5 wherein the at least one peroxyacid is selected from the group consisting of HCO$_3$H, CH$_3$CO$_3$H, C$_6$H$_4$CO$_3$H, m-ClC$_6$H$_4$CO$_3$H and mixtures thereof.

7. The method of claim 1 wherein the excess oxidizing agent is removed by a method selected from the group consisting of addition of at least one neutralizing agent, electric reduction, thermo-decomposition of the oxidizing agent and a combination thereof.

8. The method of claim 7 wherein the neutralizing agent is selected from the group consisting of H$_2$C$_2$O$_4$, hypophosphorous acid, formic acid, citric acid, ascorbic acid, NaNO$_2$, NaS$_2$O$_4$, Na$_2$SO$_3$ salts of hydrazine, R$^8$CHO, wherein R$^8$ is selected from H, alkyl of 1-20 carbons, or a phenyl or substituted phenyl group, sulfur dioxide, sodium hydrosulfite, formaldehyde sulfoxylate, diimide, hydrazine, hypophosphorous, triphenylphosphine and mixtures thereof.

9. The method of claim 1 wherein the reducing agent is hydrogen in the presence of a transition metal catalyst.

10. The method of claim 9 wherein the transition metal catalyst is selected from the group consisting of Pd/C, Pt/C, Ru/C, Rh/C, Ir/C, Ni/C, PtO$_2$, Raney Ni, Wilkinson's Catalyst and mixtures thereof.

11. The method of claim 1 wherein the method is accomplished in a single reaction vessel without isolating the Formula II compound.

12. A method comprising:
    a) oxidizing a Formula I compound with at least one peroxyacid of the formula RCO$_3$H, wherein R is H, an alkyl group of 1-20 carbons or an aryl group, to form an oxidation reaction mixture comprising a Formula II compound and a Formula II-NO compound;
    b) quenching the oxidation reaction mixture by neutralizing an excess portion of the peroxyacid of the formula RCO$_3$H with at least one neutralizing agent to form RCO$_2$H, wherein the excess portion of the peroxyacid is peroxyacid that does not react with the Formula I compound; and c) catalytically reducing the Formula II compound and the Formula II-NO compound with hydrogen in the presence of a transition metal catalyst to form a Formula III compound,

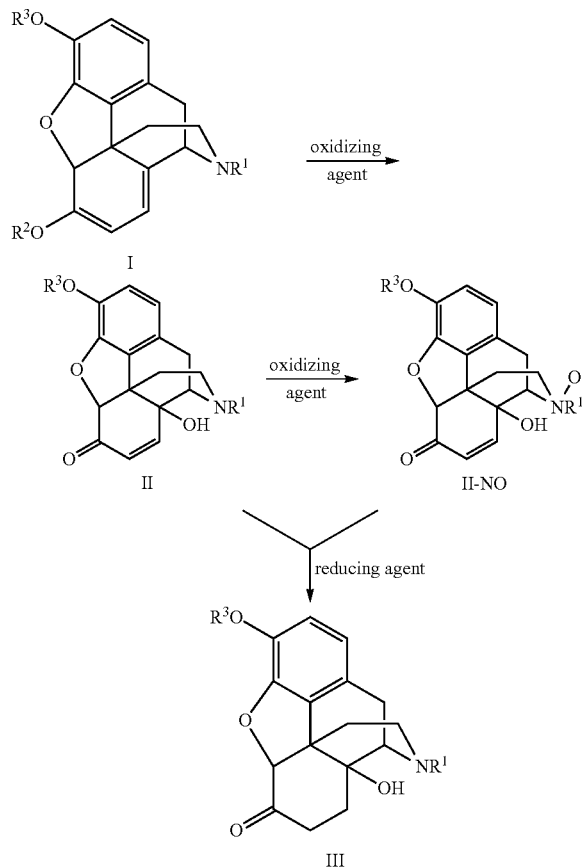

wherein $R^1$, $R^2$ and $R^3$ are independently selected from H, benzyl, 1-8 carbon alkane sulfonyl, p-tosyl, an alkyl group of 1-20 carbons, and a substituted alkyl group, wherein the alkyl group is substituted with a cyclic alkyl group, a phenyl, substituted phenyl, 1-8 carbon alkoxyl or phenoxyl groups.

13. The method of claim 12 wherein the Formula III compound formed represents greater than an 80% yield.

14. The method of claim 12 wherein the Formula III compound formed represents greater than a 90% yield.

15. The method of claim 12 wherein the Formula III compound formed represents greater than a 95% yield.

16. The method of claim 12 wherein the at least one peroxyacid includes a peroxyacid selected from the group consisting of $HCO_3H$, $CH_3CO_3H$, $C_6H_4CO_3H$, m-$ClC_6H_4CO_3H$ and mixtures thereof.

17. The method of claim 12 wherein the neutralizing agent is selected from the group consisting of $H_2C_2O_4$, hypophosphorous acid, formic acid, citric acid, ascorbic acid, $NaNO_2$, $NaS_2O_4$, $Na_2SO_3$, salts of hydrazine, $R^8CHO$, wherein $R^8$ is selected from H, alkyl of 1-20 carbons, or a phenyl or substituted phenyl group, sulfur dioxide, sodium hydrosulfite, formaldehyde sulfoxylate, diimide, hydrazine, hypophosphorous, triphenylphosphine and mixtures thereof.

18. The method of claim 12 wherein the at least one transition metal catalyst is selected from the group consisting of Pd/C, Pt/C, Ru/C, Rh/C, Ir/C and Ni/C, $PtO_2$, Raney Ni, Wilkinson's Catalyst and mixtures thereof.

19. The method of claim 12 wherein the method is accomplished in a single reaction vessel without isolation of the Formula II compound.

20. A method for producing oxymorphone comprising:
a) oxidizing oripavine with a peroxyacid acid $RCO_3H$, wherein R is H, an alkyl group or an aryl group, to form an oxidation reaction mixture comprising 14-hydroxymorphinone and 14-hydroxymorphinone N-oxide;
b) quenching the oxidation reaction mixture by neutralizing an excess portion of the peroxyacid with a neutralizing agent, wherein the excess portion of the peroxyacid is peroxyacid that does not react with the oripavine; and
c) catalytically hydrogenating the 14-hydroxymorphinone and 14-hydroxymorphinone N-oxide with a reducing agent to form oxymorphone.

21. The method of claim 20 wherein the oxymorphone formed represents greater than an 80% yield.

22. The method of claim 20 wherein the oxymorphone formed represents greater than a 90% yield.

23. The method of claim 20 wherein the oxymorphone formed represents greater than a 95% yield.

24. The method of claim 20 wherein the peroxyacid includes a peroxyacid acid selected from the group consisting of $HCO_3H$, $CH_3CO_3H$, $C_6H_4CO_3H$, m-$ClC_6H_4CO_3H$ and mixtures thereof.

25. The method of claim 20 wherein the neutralizing agent is selected from the group consisting of $H_2C_2O_4$, hypophosphorous acid, formic acid, citric acid, ascorbic acid, $NaNO_2$, $NaS_2O_4$, $Na_2SO_3$, salts of hydrazine, $R^8CHO$, wherein $R^8$ is selected from H, alkyl of 1-20 carbons, or a phenyl or substituted phenyl group, sulfur dioxide, sodium hydrosulfite, formaldehyde sulfoxylate, diimide, hydrazine, hypophosphorous, triphenylphosphine and mixtures thereof.

26. The method of claim 20 wherein the reducing agent is hydrogen in the presence of a transition metal catalyst selected from the group consisting of Pd/C, Pt/C, Ru/C, Rh/C, WC, Ni/C, $PtO_2$, Raney Ni, Wilkinson's Catalyst and mixtures thereof.

27. The method of claim 20 wherein the method is accomplished in a single reaction vessel without isolating the 14-hydroxymorphinone.

* * * * *